United States Patent [19]

Linkow et al.

[11] Patent Number: 4,932,868
[45] Date of Patent: * Jun. 12, 1990

[54] SUBMERGIBLE SCREW-TYPE DENTAL IMPLANT AND METHOD OF UTILIZATION

[75] Inventors: Leonard I. Linkow, New York, N.Y.; Anthony W. Rinaldi, Philadelphia, Pa.

[73] Assignee: Vent-Plant Corporation, Philadelphia, Pa.

[*] Notice: The portion of the term of this patent subsequent to Dec. 15, 2004 has been disclaimed.

[21] Appl. No.: 319,651

[22] Filed: Mar. 6, 1989

Related U.S. Application Data

[63] Continuation of Ser. No. 25,942, Mar. 16, 1987, Pat. No. 4,842,518, which is a continuation-in-part of Ser. No. 904,381, Sep. 4, 1986, abandoned.

[51] Int. Cl.⁵ .............................................. A61C 8/00
[52] U.S. Cl. .................................................... 433/174
[58] Field of Search ................................ 433/173, 174

[56] References Cited

U.S. PATENT DOCUMENTS 3,579,831  5/1971  Stevens .............................. 433/174

Primary Examiner—Robert Peshock
Attorney, Agent, or Firm—Darby & Darby

[57] ABSTRACT

A submerigible screw-type implant includes a longitudinal channel which directs bone chips towards the base of a bore in the patient's bone in which the implant is installed. These bone chips promote autogenous rapid regrowth of new bone to securely anchor the implant in place. In order to be able to position the implant at the most advantageous angle at the edentulous sight, angled abutments for supporting an artificial tooth structure or angularly adjustable abutments are provided. The angularly adjustable abutments may be in the form of a ball and socket joint in which the socket includes an inner casing having a peripheral extension that acts to lock the joint at the desired angle. Also, the support for an artificial tooth may include a shock-absorbing cushion to prevent some of the forces of mastication from disturbing the implant.

3 Claims, 5 Drawing Sheets

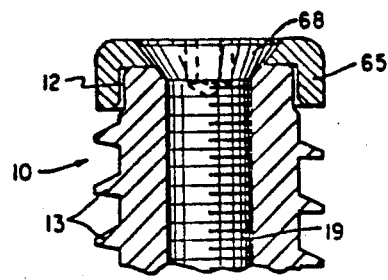
FIG. 12
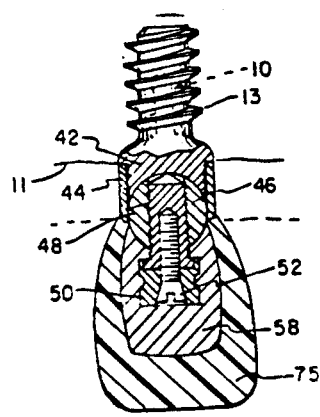 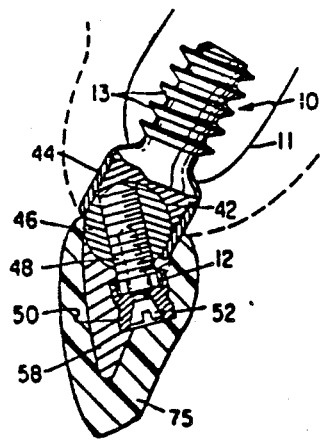
FIG. 13   FIG. 14

SUBMERGIBLE SCREW-TYPE DENTAL IMPLANT AND METHOD OF UTILIZATION

This is a continuation of application Ser. No. 025,942, filed Mar. 16, 1987, now U.S. Pat. No. 4,842,518, issued June 27, 1989, which is a continuation-in-part of Patent Application Ser. No. 904,381 filed Sept. 4, 1986and now abandoned.

TECHNICAL FIELD

This invention relates to dental implants and, more particularly, to submergible screw-type implants

BACKGROUND ART

Screw-type implants are well known in the art. U.S. Pat. No. 3,499,222 of L. I. Linkow et al. discloses screw-type implants which may be buried in the alveolar ridge crest bone of a patient in an edentulous region. The implant has a threaded lower portion which may be screwed into an opening created in the bone after the tissue has been displaced. A coronal portion protrudes above the bone and is used to support an artificial dental appliance, e.g. an artificial tooth or bridge.

In more recent year's submergible implants have been created in which the threaded portions of the implants can be completely embedded in the bone. They may then be covered with tissue and allowed to remain in place while new bone grows around the implant and through vent holes in it. Once it is firmly anchored in new bone (3 to 6 months), the tissue is reopened and an upper post portion is screwed into the implant portion and is used to mount the artificial dental device.

It is advantageous when installing an implant portion in the patent's bone, if the implant is self-tapping in a bore created in the bone. This causes it to be anchored better. Also, it would be advantageous if the bone chips created during a self-tapping operation were deposited into the bore or opening because these chips promote faster bone growth because of their autogenous nature.

In order to align the artificial tooth or other dental devices with the other teeth of the patient, it may be necessary to have the post portion at an angle to the implant portion. This may be accomplished by bending the post portion so that its head is at an angle to the threaded shaft. This bending may be accomplished before the post is threaded into the implant portion or afterward. If the post is bent before attachment to the implant, the proper alignment is difficult to achieve. If bent after attachment, there is a danger that too much stress will be put on the implant portion and it will loosen in the bone and fail. Also bending the post may fatigue the metal of the post and cause breakage.

DISCLOSURE OF THE INVENTION

The present invention is directed to a dental implant which, in its preferred form, is of the submergible screw type with a longitudinal channel or slot through the threads so as to improve their self-tapping ability. The implant also has an angled swivelable connector to allow the post for supporting an artificial dental appliance to be positioned in proper alignment with other teeth in the patient's mouth without applying stress to the implant.

In an illustrative embodiment of the invention, the implant portion of the device includes a threaded region that contains a longitudinal channel through a portion of the outer parts of the threads. The channel is wider toward its bottom. One side of the channel is at a right angle to the implant circumference so as to create a cutting edge that assists in the formation of a self-tapping capability for the implant when it is installed in a bore or opening in the patient's bone. The other side of the channel is at an oblique angle to the circumference.

The channel guides bone chips created during the threading of the implant toward the base of the bore in the bone. By terminating the channel below the uppermost threads, epithelial tissue is prevented from growing down into the bone along the channel.

The post or abutment portion of the implant which supports an artificial dental appliance may be a straight portion on to which the appliance is threaded. However, in situations where it must be at an angle to the implant portion the abutment may be a separate piece from the implant portion and may be attached thereto at an angle by means of a connection portion of the abutment. The connection portion may be in the form of a rotatable beveled collar, a ball and socket joint, or other suitable means that allow the post to swivel about the axis of the implant portion and/or to assume various angles with respect to that axis. Once in place, means are provided for securing the abutment against further movement with respect to the implant portion. As a result the implant can assume a desired angle to assure proper alignment of the artificial dental structure with the other teeth of the patient along the occlusal plane.

In one version the abutment may include an elastic ring This ring flexibly separates an upper portion and lower portion of the abutment, much in the manner of a shock absorber. With this arrangement some of the shock of mastication is buffered so that it is not applied directly to the screw implant.

The present invention also contemplates a unique surgical method. With this method an incision is made in the tissue covering the alveolar ridge crest bone. This underlying bone is then exposed and a bore is drilled into the bone at a depth sufficient to hold the implant portion of the device. The bore is made slightly smaller in diameter than the implant device and is at an angle which will allow it to engage the major portion of the available bone. Then the implant device is threaded into the remaining bone about the bore utilizing its self-tapping threads and the self-tapping feature of the channel along its length. It is typically buried at a depth such that it is submerged below the upper surface in the bone and is completely buried in the bone.

During the insertion procedure bone chips are removed from the walls of the bore while forming the grooves in the bone which match the threads in the implant. These bone chips drop along the channel to the base of the bore and help to promote growth of new bone which firmly anchors the implant in place.

Threading of the implant portion into place may be accomplished with a hexagonal projection or recess located at the free end of the implant portion. This hexagonal section is connected to a wrench-type device to screw the implant into the bone.

Once secured in place a cover of minimal height may be attached to the exposed surface of the implant portion by a screw passing through the cover and threaded into an aperture in that surface. The tissue may then be sutured over the implant cover. New bone is allowed to grow and to anchor the cover and implant firmly in place. Several weeks or months later, the tissue is opened again and the cover is removed. A threaded abutment or post is then attached to the threaded aperture in the end of the implant portion. This abutment is used for supporting the artificial dental appliance.

The angle at which the implant portion is located in the bone may not be the most conducive to the proper alignment of the artificial tooth or other dental devices with the remaining teeth of the patient. As a result, the abutment includes an angled, swivelable connection portion for attaching the abutment to the implant portion. In one embodiment fixed angular devices which are rotatable about the longitudinal axis of the implant are utilized, and in another embodiment the part is continuously swivelable to any desired angle. In either case, after the abutment or support for the artificial tooth is at the proper angle, it is locked such that it remains in that position. Finally, the tissue is closed about the abutment an the artificial tooth or bridge support is cemented or screwed to the abutment.

BRIEF DESCRIPTION OF THE DRAWINGS

The foregoing and other features of the present invention will be more readily apparent from the following detailed description and drawings of illustrative embodiments of the invention, in which:

FIG. 12 is a side view of a healing collar according to the present invention;

FIGS. 13 and 14 are front and side sectional views of an artificial tooth with an abutment according to FIG. 7;

DESCRIPTION OF ILLUSTRATIVE EMBODIMENTS

Figure 1:
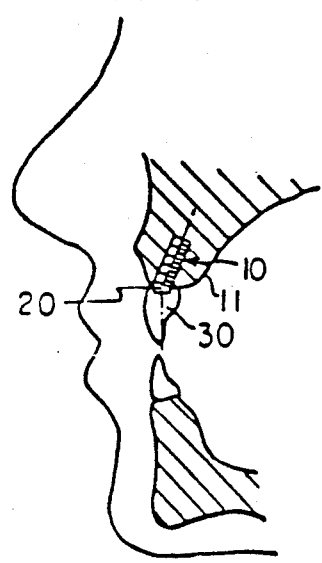
FIG. 1 is a schematic cross section of the side of a patient's face showing the alveolar ridge crest with a screw type implant according to the present invention installed therein.

The present invention contemplates at least a two part screw-type dental implant, i.e, an implant portion 10 which is buried in the bone of the patient and a post or abutment portion 20 which is attached thereto and which supports an artificial tooth structure 30. As shown in FIG. 1, an implant screw portion 10 is located in a bore in the aveolar crest 11 at an angle that causes it to be in the center of the thickest portion of good available bone. The abutment 20 is attached both to the implant portion 10 and the artificial tooth 30, and is set so that the tooth is at an angle to the implant which causes the tooth to be in proper alignment.

Figure 2:
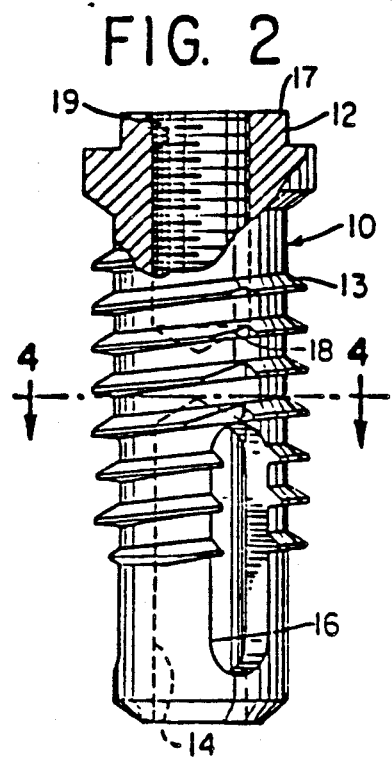
FIG. 2 is an enlarged view of an illustrative embodiment of the implant portion of the device of FIG. 1 with an external hex projection.
Figure 3:
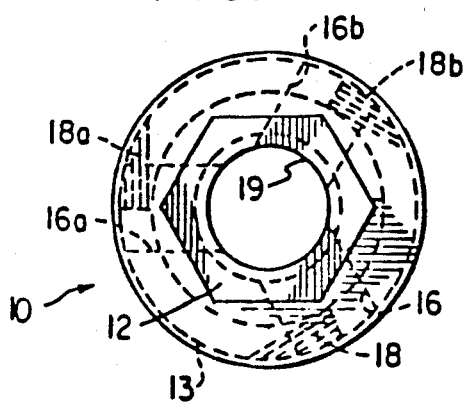
FIG. 3 is a top view of the implant portion of FIG. 2 showing the external hex portion.

In FIGS. 2 and 3 the screw implant portion 10 of FIG. 2 is illustrated in more detail. This implant portion 10 contains threads 13 which extend over the middle region of the implant portion. These threads may have a flat bottom and be angled up to form a Christmas tree shape in cross section. The lower half of the implant portion 10 contains a cavity 14 (shown in dotted line). Also, spaced about the lower end of the implant are holes or vents 16, 16a and 16b, which penetrate from its exterior to the interior cavity 14. The purpose of these vents is to allow new bone to grow through and into the center cavity in order to firmly anchor the implant in the patient's bone. The upper surface 17 of the implant portion defines a threaded aperture 19 which is used to connect the abutment 20 to the implant portion 10. The projecting structure 12 which forms surface 17 has a hexagonal shape as shown more clearly in FIG. 3. This hexagonal shape allows a tool, e.g. a wrench, to be used to rotate the implant portion so as to thread it into the patient's bone.

Figure 4:
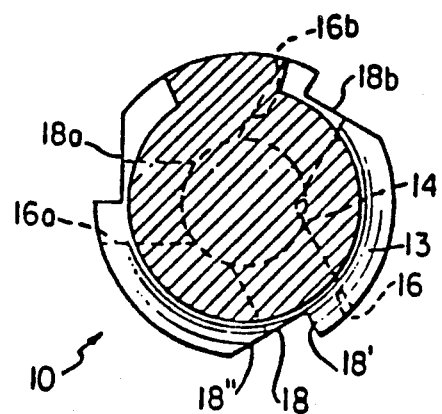
FIG. 4 is a cross-sectional view through the implant portion of FIG. 2 along line 4—4 showing the cross-sectional shape of the channel according to the present invention.

According to the present invention a channel 18 is cut through the threads 13 and possibly into the outer casing of the implant portion 10. As depicted in dotted line in FIG. 3 and in cross-section in FIG. 4, the channel 18 is one of three channels 18, 18a, 18b in a typical implant portion. These channels are made to intersect the respective vents 16, 16a and 16b which are spaced at angles of 120 about the circumference of the implant portion 10. The channels do not extend completely toward the upper surface 12 in order to prevent tissue from growing down along the channel, and to prevent the incursion of food and bacteria. It should be particularly noted in FIG. 4 that the channels 18 have one edge which is at about 90° to the circumference of the implant, i.e., surface 18', and another more obliquely shaped edge, i.e. surface 18".

During installation of the implant, an incision is made in the gum tissue of the patient and the underlying bone is exposed. Then a drill or burr is used to make an opening or bore hole in the bone which is slightly larger in diameter than the implant portion body 10, but which is not as wide as the threads 13. A wider counterbore may be provided to accommodate a protection collar as explained subsequently. Next the implant is inserted up to the first thread in the opening in the bone. A tool, such as a wrench, is used to engage the hex portion 12 and to rotate the implant. The threads 13 are made to be self-tapping so that the implant portion will begin to screw down into the patient's bone. If necessary, a bone tap can be used to create grooves in the hard upper cortical bone prior to insertion of the implant portion. The right angle surface 18' of the channel also has self-tapping properties so as to ease the insertion of the implant, once it has reached the depth of the channels 18. Further turning of the implant causes the right angle surface 18' to scrape off bone as the implant is being threaded and to push the resulting bone chips forward. This causes the bone chips to fall through the channels 18 and into the area of the vents 16 where they may penetrate into the interior cavity 14. To facilitate this, the channels 18 are made wider towards the vents 16.

As a result of this structure, bone chips created during the implant procedure tend to accumulate at the base of the implant in the patient's bone. Because of the autogenous nature of these bone chips they promote the growth of new bone in the area and speed the formation of new bone around and through the implant such that it is anchored in place more rapidly.

Figure 5:
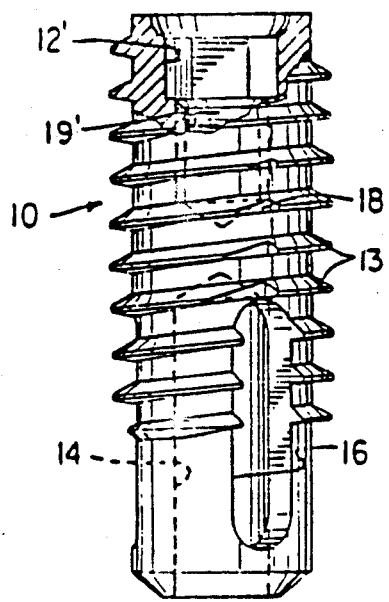
FIG. 5 is an implant portion of a screw-type implant according to the present invention with an internal hex recess.

In FIG. 5 there is shown an implant portion 10 which is nearly identical to that shown in FIG. 1. The principal difference is that, rather than having a hexagonal projection useful for applying torque to the implant, a hexagonal recess 12' is provided. In addition, the threaded aperture 19' is made somewhat smaller and is located at the base of hexagonal recess 12'. As explained previously, the threaded aperture 19' is used for attaching the implant portion of the device to the abutment portion One embodiment of such an attachment is shown in FIG. 6.

Figure 6:
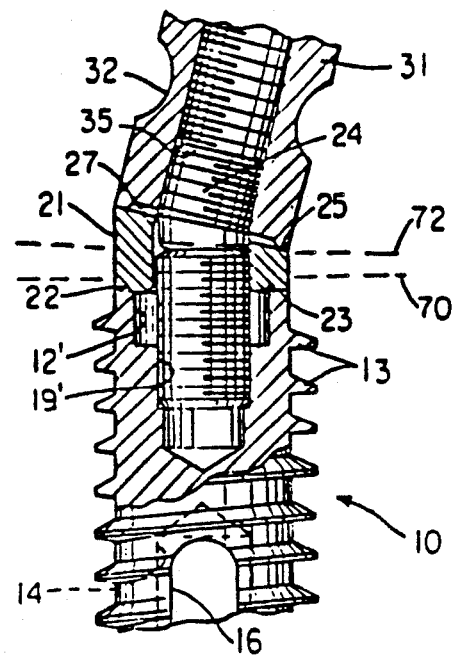
FIG. 6 is a illustrative embodiment of a completed screw-type implant with an angularly positioned threaded shaft attached thereto.

In FIG. 6 the upper part of the implant portion 10 is shown partly broken away and partly in section. It is shown partly broken away to exhibit the interior cavity 14 and the threads 13. Towards the upper part of the implant portion it is shown in cross section. This implant portion is like that shown in FIG. 5 with a hexagonal recess 12' for rotating it into position in the bone. As shown in FIG. 6 the screw type implant portion 10 is connected to an abutment portion 20 that includes a transitional collar 21, an angled threaded shaft 24, and a tooth support cylinder 31. The threaded shaft 24 has its lower end screwed into threaded aperture 19' in the implant portion 10. The upper end of the threaded shaft, which is set at an angle to the lower end, is received within a threaded aperture 35 in tooth support cylinder 31. This cylinder 31 contains a recessed portion 32 which may be utilized in fixing on to the cylinder via cement or some other convenient and well known method, a porcelain, plastic, or other dental tooth-colored veneering material in the form of an artificial tooth.

The transitional collar 21 is located between the upper end of the implant portion 10 and the cylinder 31. This collar has an angled upper surface 25 and a perpendicular lower surface 23. The angle of the upper surface is made to equal the angle of the upper part of the angled shaft 24. While collar 21 surrounds threaded shaft 24, it does not engage its threads.

During an installation procedure the implant portion 10 is located in the patient's bone as previously described. The gingival tissues can then be replaced over the implant portion and several weeks or months allowed to pass while new bone grows around and through the implant portion. However, alternatively the artificial tooth can be connected to the implant immediately. Whichever manner is chosen, the attachment is accomplished by selecting an angled shaft and transition collar which have an angle which will cause the artificial tooth to be correctly aligned with the other teeth of the patient. Therefore the dentist or oral surgeon must be provided with a variety of such shafts and collars which are at standard angles. Also during the insertion procedure the surgeon must appropriately angle the opening in the bone so it penetrates a reasonably thick area of good bone. This may require that the opening in the bone be drilled at an angle in order to avoid penetrating a nearby sinus cavity, passing completely through the bone, or contacting a nerve bundle. However, in selecting the angle at which the implant is buried, care must be taken to make sure that this angle will accommodate one of the standard angles available with the threaded shafts and collars, e.g. 10, 20 or 30 degrees, so as to result in alignment between the new artificial tooth and the remaining teeth of the patient.

Once the threaded shaft 24 is engaged with the implant portion 10, the collar 21 is slipped over the free end of the shaft. Then the shaft is rotated so that it is firmly secured in the implant portion and is extending in the proper direction. With the collar in place over this shaft, the cylinder portion 31 is threaded over the open or free end of the shaft until it makes tight contact with the upper surface of the collar and begins to squeeze the collar between the cylinder and implant portions. Notches and recesses 22 and 27 are provided in the mating surfaces such that, once the parts are screwed together, these notches and recesses engage each other and prevent unintentional unscrewing of the portions of the implant. With this firm attachment completed, the artificial tooth can then be attached over the abutment cylinder 31.

In FIG. 6 the level the patient's bone is shown as dotted line 70. Since the implant portion is submerged in the bone, the line 70 intersects the lower portion of the transitional collar 20. The gum tissue line 72 is towards the upper portion of the transitional collar. As a result the collar acts a barrier to prevent the encroachment of bacteria and food into the interior portion of the collar and the hex recess of the implant portion.

With the embodiment of FIG. 6 fixed angles are provided to the dentist and he must work with the standard angles and the angle which he creates for the bore in the patient's bone, in order to assure proper alignment of the teeth. In some patients who have had serious bone disease, the amount of available good bone is limited and the dentist has only a limited amount of freedom in selecting the angle at which the bore for the implant is made. Also with the embodiment of FIG. 6 it is necessary for a dentist to keep a stock of various angled shafts and collars. The difficultly presented by the type of implant in FIG. 6 is overcome by the implant shown in FIG. 7.

Figure 7:
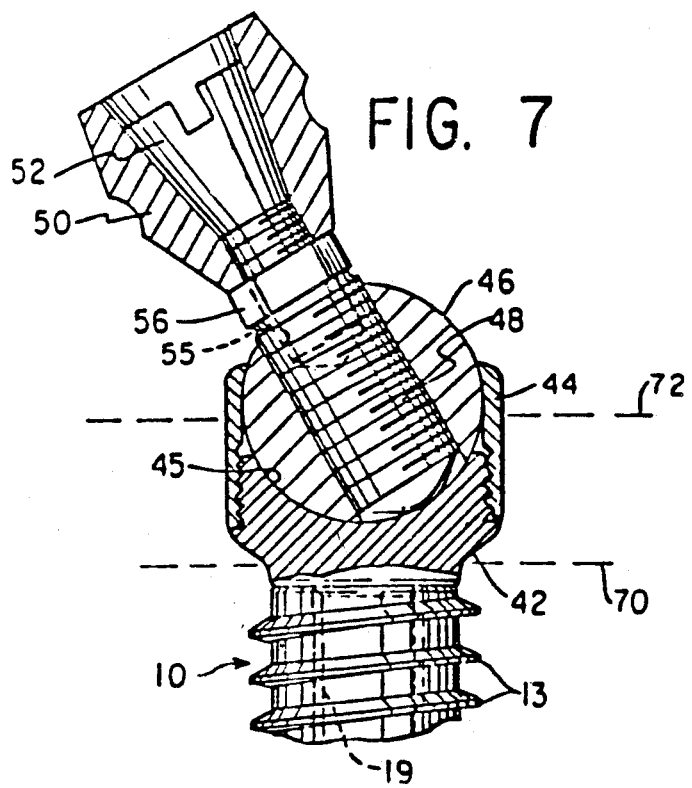
FIG. 7 is a cross-sectional view of a ball and socket connection portion of an abutment according to the present invention.

In FIG. 7 the angled shaft and transition collar are replaced with a ball and socket joint which allows for the setting of the angled relationship between the implant portion and the abutment portion at any selected angle within the range of motion of the ball and socket joint, e.g. up to 30–40 degrees. In FIG. 7 the threaded cavity 19 receives the threaded shaft of a lower or inner abutment casing 42. This casing has a generally Y-shape with the lower portion being the shaft that extends into and engage the threads of cavity 19. The upper portion of casing 42 has a hemispherical surface 45 such that it can receive a ball 46. An upper or outer casing 44 screws onto outer threads of the inner casing 42 such that ball 46 is wrapped within the abutment casing, but is free to rotate therein so as to create a ball and socket joint.

A relatively large set screw 48 penetrates the ball completely. This set screw 48 has an internal threaded cavity 55 which passes through an upper hexagonal projection 56. Once the implant portion 10 has been located in the bone at the optimal angle, the ball 46 is rotated such that the center axis of the set screw is at the proper angle for mounting of an artificial tooth in line with other teeth in the patient's mouth. Then the hexagonal portion 56 is rotated with a wrench or other tool so the set screw comes into extreme frictional contact with the hemispherical surface 45 of inner casing 42. This prevents further rotation of the ball and the set screw.

The artificial tooth structure in the embodiment of FIG. 7 has an interior cylinder 50, about which the porcelain, plastic or other dental material is formed to create the artificial tooth structure. This cylinder 50 with the artificial tooth structure mounted thereon, is placed on top of the hexagonal projection 56 and is then attached thereto by means of a screw 52 which passes through the cylinder 50 and into the threaded aperture 55 in set screw 48.

The bone line 70 is shown in FIG. 7 as being approximately mid-way through the lower abutment casing 42, while the gum line 72 is just below the upper edge of the outer or upper casing 44. Thus, the bone does not interfere with the setting of the proper angle for the abutment and the tissue is not likely to contact moveable adjustment parts.

Figure 8:
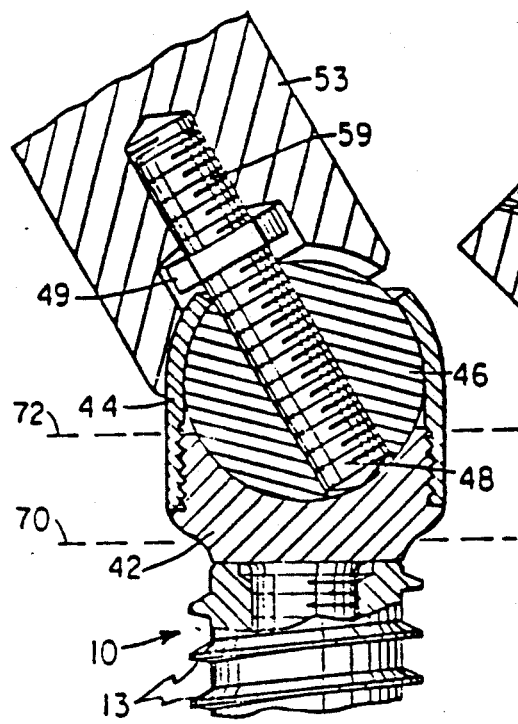
FIG. 8 illustrates a modification of the ball and socket joint of FIG. 7.

The arrangement of FIG. 8 is a modification of that shown in FIG. 7. In this arrangement the set screw 48, which has a threaded recess 55 at its end in FIG. 7, is replaced with a set screw 49 that has a further screw thread 59 on the opposite side of the hex projection 56. This additional screw thread is used to mount an artificial tooth support cylinder 53 which has an interior threaded cavity. However, this device is essentially located and fixed in position in the same manner as the implant of FIG. 7. One difference with this implant of FIG. 8 is that the artificial tooth support cylinder 53 may extend down to and in contact with the outer casing 44. This is done above the gum tissue line 72 as shown in the figure. Because of the contact between the cylinder and the casing 44, food and bacteria are prevented from entering between these two parts and the likelihood of infection is reduced. However, this arrangement allows for somewhat less range of angular adjustment. In particular the arrangement of FIG. 7 is capable of an angular adjustment range of approximately 37 ½°, while that of FIG. 8 is limited to about 30°.

As a further alternative, the set screw 48, rather than having a projecting threaded portion located above the hexagonal adjustment nut 56, may have a projecting cylinder which is internally threaded (not shown). Thus either a male or female connection of this type may be used without difficulty.

Figure 9:
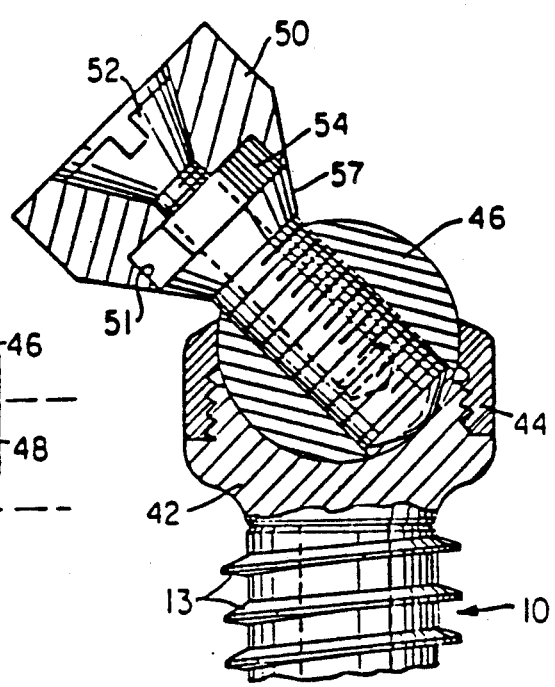
FIG. 9 illustrates a further modification of the ball and socket joint of FIG. 7.

In order to get increased angular adjustment, an arrangement such as that shown in FIG. 9 may be used. The abutment arrangement of FIG. 9 is essentially the same as that of FIG. 7; however, the ball and socket joint are made smaller and the ball sits higher in the socket joint. Further, the set screw 54 of FIG. 9 is made to have a beveled surface 57 such that a greater angular rotation may be made before it contacts the upper part of the outer casing 44. With this arrangement nearly 45 degrees of angular adjustment can be achieved.

The abutment cylinder 50 has a recess 51 to receive the outer end of the set screw 54. This allows for greater stability when it is attached to the set screw by means of attachment screw 52. The cylinder 50 is also angled in the same manner as the surface 57 of the set screw 54 so that it does not bind against the upper abutment casing 44 and limit angular rotation.

Figure 10:
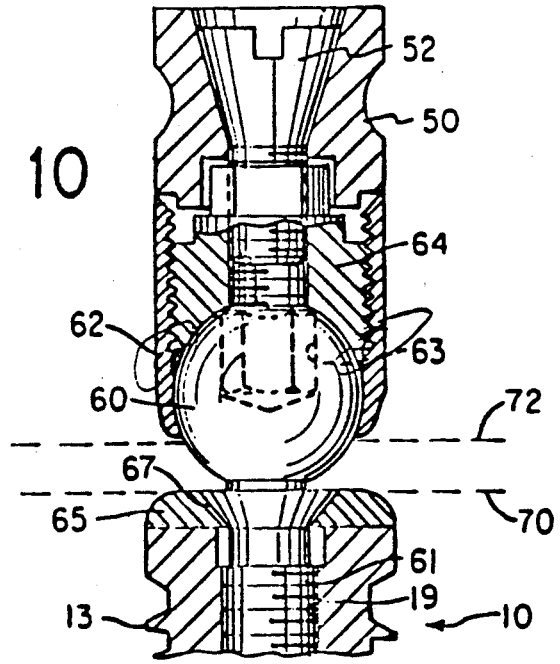
FIG. 10 is a ball and socket joint connection portion with a stationary ball.

In FIG. 7-9 the ball rotates with the set screw during angular adjustment. However, as an alternative, the ball may remain stationery and the abutment casing may rotate as shown in FIG. 10. In FIG. 10 a threaded ball joint 60 has a projecting threaded shaft 61 which is received in threaded recess 19 of the implant portion 10. Various size protection washers or collars 65 can be located about the finial part 67, which connects the ball to the threaded shaft, in order to cover the upper surface of whatever implant portion is used, thereby preventing bacteria and food from entering the bore. The opening in the bone can be countersunk as indicated by dotted line 70 so the collar can extend out beyond the implant portion upper surface, and bone can grow over part of the upper surface of the collar.

A two-part casing 62, 64 is mounted on the ball 60. The casing includes outer casing portion 62, which secures the remote end of the ball, and an inner casing 64, which provides the main hemispherical surface against which the outer casing holds the ball in a rotatable manner. These two casing parts can be threaded together or attached to each other in any convenient manner. Their attachment, however, is such that the casing may rotate freely on the ball.

At the opposite end of ball 60 from the screw threads is a hexagonal recess 63, which is the means by which this threaded ball joint is screwed into the threaded recess 19 of the implant portion. In this arrangement the gum line 72 is shown about ⅓ up from the base of the ball joint, but below the lower extension of casing 62.

A hexagonal projection 66 is provided on the inner casing 64. This projection can be used to rotate the inner casing 64 so that the ball is squeezed between it and the outer casing 62 so that swiveling can be prevented when the arrangement is at the proper angle. A conventional cylinder 50 for a dental prosthesis is attached to the inner casing 64 by means of a screw 52. This screw 52 penetrates a threaded aperture in the inner casing.

Figure 11A:
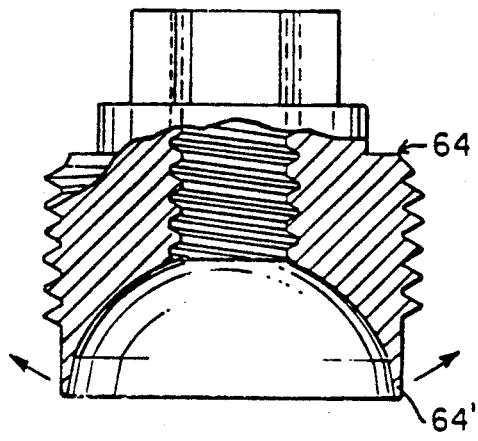
FIGS. 11A and 11B are cross-sectional views of a unitary inner casing and a two-part inner casting, respectively.

An enlarged view of the inner casing 64 is shown in FIG. 11A. The lower peripherial extension 64, of this casing forms a wedge that projects between the ball 60 and the outer casing 62 as shown in FIG. 10. When the inner casing 64 is screwed down onto ball 60, the extension 64, acts to lock the abutment on the ball and prevents further rotation. In part this locking is maintained due to the fact that the diameter of the extension 64' is slightly less that the distance across the ball at its location. As a result there is an outward flaring of the extension as shown by the arrows in FIG. 11A, which prevents the unthreading of inner casing 64.

Figure 11B:
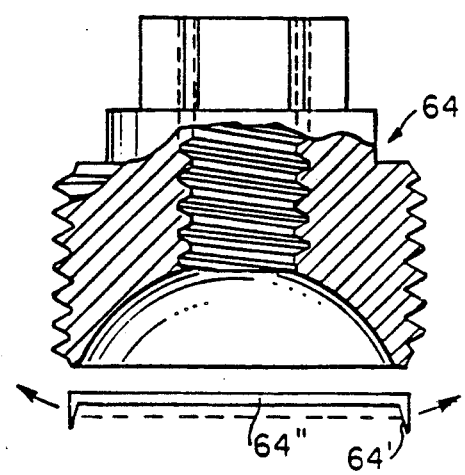

Instead of a one piece casing as shown in FIG. 11A, the inner casing may be in two parts as shown in FIG. 11B, where the extension 64' is part of a locking ring or washer 64". With this arrangement the ball is surrounded by the ring 64" and the casing 64. As the casing is threaded into contact with the ball it forces the ring to wedge between the ball 60 and the outer casing to frictionally hold the ball. The outward flaring of the extension at the end of this compression process tends to prevent the unthreading of the inner casing, which prevents the abutment from becoming loose.

Installation of submergible implants is generally a two stage procedure. During the first stage the implant portion is buried in the bone and the tissue is restored in place over it. Time is allowed to pass while new bone grows about, and often over, the implant. The tissue is then reopened at the start of the second stage. If bone has grown over the submerged implant, it must be removed by a burr before the abutment can be installed. If the bone grows into the threaded aperture for the abutment, however, removal of this bone may be very difficult. Consequently, it is conventional to install a thread cap having a low height into the aperture during the first stage. However, bone also grows over this cap and it must be removed in order to replace the cap with the abutment. Removal of such bone may cause some loosening of the implant portion.

With the present invention, the collar 65 is used with a screw 68 as a temporary cap as shown in FIG. 12. Even if bone grows up over the edges of the collar 65, there is no need to remove it because it becomes part of the permanent abutment. In particular cover screw 68 is removed during the second stage operation, which may require the removal of a small amount of bone that has growth over the screw. Then the cover screw 68 is replaced with threaded shaft of abutment ball 60 which has the abutment casings 62, 64 already installed. Thus the collar 65 which is anchored in bone, need not be freed from the bone as in prior art caps, but becomes part of the final abutment structure.

FIGS. 13 and 14 show front and side sectional views of an incisor of a patient which is supported by an implant according to the present invention. As can be seen, particularly from FIG. 14, the patient's upper front jaw bone has only a thin amount of good bone 11 and this bone is at an angle to the regular alignment of the other incisors in the patient's mouth. Utilizing the present invention, implant portion 10 is located in the center of the main portion of this bone. After this implant portion 10 is firmly anchored in good bone, either immediately after its insertion or after several weeks or months have been allowed to pass, the abutment portion is installed. The abutment portion is a ball and socket joint like that in FIG. 7 having a set screw 48 which locks the ball 46 at the proper angle. The cylinder 50 of the artificial tooth support is then attached to the set screw via an attachment screw 52. As shown in cross section in FIG. 14, cast metal 58 surrounds cylinder 50 and a porcelain or plastic dental material 70 forms the tooth structure about the metal.

Figure 15:
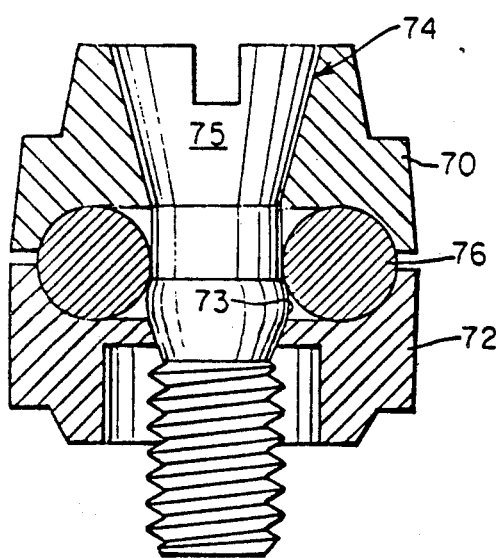
FIG. 15 is a cross-sectional view of an embodiment of an abutment with a shock-absorbing cushion.

FIG. 15 illustrates a cross-sectional view of an abutment with shock-absorbing capabilities. This abutment may be adapted for use with any of the previously discussed implants and angular adjustment devices.

The abutment of FIG. 15 has a cylinder portion 70, upon which the artificial tooth is mounted. In addition it has a collar 72. The cylinder and collar are connected by a screw 74. Screw 74 also acts to connect the cylinder and collar 70,72 to the rest of the abutment in much the same way as screw 52 connects cylinder 50 to the rest of the implants in FIGS. 7, 9 and 10.

A flexible buna rubber washer 76, such as that used for over dentures, is located between and separates the cylinder 70 and collar 72 so that the cylinder 70 may move with respect to the collar 72. Typically, the artificial tooth will be mounted only on the cylinder 70. As a result, some of the forces applied to the artificial tooth during chewing or biting are absorbed by the flexible washer 76 and are not transmitted to the collar 72 and the rest of the implant.

In order to make it easy to install the washer 76, the cylinder and collar parts are formed such that they define an oval recess which seats the washer. The head 75 of the screw 74 and a peripheral flare 73 on the screw tend to keep the washer within the oval recess.

During installation the washer is assembled between the cylinder 70 and collar 72. Then the screw 74 is pushed down through the opening in the cylinder part. The flare 73 compresses the washer 76 slightly as it passes through the washer. Then the screw 74 is passed through collar 72 and threaded into the rest of the implant. At some point, the flare 73 is drawn against the opening in collar 72. However, the threading operation is continued in order to wedge the flared part of screw 74 into collar 72. This acts to keep screw 74 from unthreading after the artificial tooth is put into use.

Figure 16:
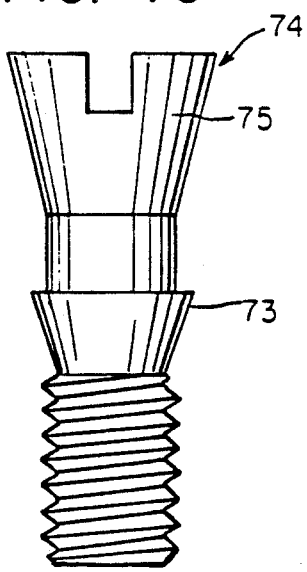
FIG. 16 is an alternative embodiment of the screw of the shock-absorbing abutment of FIG. 15.

FIG. 16 shows an alternative version of the screw 74 of FIG. 15. In this alternative, the flared part 73 has a triangular cross-sectional shape. Once this screw has been pushed through the washer 76, it cannot be withdrawn. Thus, it is necessary to cut the washer to remove it.

Besides being used to mount a single tooth, the implants according to the present invention can be used as supports for a permanent bridge or a removable bridge. In the case of a removable bridge the abutment cylinder is in the form of small copings which can be spaced throughout the edentulous span of a patient. These copings support a bar onto which the bridge structure may be screwed or clipped.

While the invention has been particularly shown and described with reference to preferred embodiments thereof, it will be understood by those skilled in the art that various changes in form and details may be made thereon without departing from the spirit and scope of the invention.

What is claimed is:

1. An implant portion of an implant designed for supporting a prosthetic structure comprising:
   an implant body having threads over at least part of its exterior surface and being adapted to be threaded into an opening in a bone of a patient which bone has been exposed by an incision in the covering tissue; and
   at least one channel formed such that it at least extends through threads on the body for directing bone chips toward a base portion of the opening in the bone, one edge of the threads at one side of the channel being substantially at a right angle to the circumferential direction of the threads, said one edge being adapted (i) to promote self-tapping of the threads in the bone, (ii) to shave off pieces of bone during threading of the implant portion into the bone, and (iii) to direct the pieces of bone into the channel such that the channel may direct pieces toward the base portion of the opening.

2. An implant portion of an oral implant designed for supporting an artificial tooth structure comprising:
   a generally cylindrical implant body having a plurality of circumferential projections extending over at least part of its exterior surface and being adapted to be installed in an opening in the bone of a patient by rotation thereof at least in part; and
   at least one channel formed such that it extends generally longitudinally through the projections of the body for directing bone chips towards a base portion of the opening in the bone, one edge of the projections at one side of said channel being substantially at a right angle to the circumferential direction of the implant body, said one edge being adapted (i) to promote self tapping of the projections in the bone during rotation of the body, (ii) to shave off pieces of bone during rotation of the implant body, and (iii) to direct the pieces of bone into the channel such that the channel may direct the pieces toward the base portion of the opening.

3. An implant as claimed in claim 2 wherein the projections are threaded and the implant portion is installed by threading it into the opening in the bone.

* * * * *

UNITED STATES PATENT AND TRADEMARK OFFICE
CERTIFICATE OF CORRECTION

PATENT NO. : 4,932,868
DATED : June 12, 1990
INVENTOR(S) : Leonard I. Linkow and Anthony W. Rinaldi It is certified that error appears in the above-identified patent and that said Letters Patent is hereby corrected as shown below:

<u>Title page,</u>
Item [*], should read -- this patent is subject to a terminal disclaimer --

Signed and Sealed this

Seventeenth Day of June, 2003

JAMES E. ROGAN
*Director of the United States Patent and Trademark Office*